United States Patent [19]

Jorda et al.

[11] Patent Number: 5,585,050
[45] Date of Patent: Dec. 17, 1996

[54] MICROCAPSULES CONTAINING AT LEAST ONE ACTIVE INGREDIENT, APPLICATION OF SUCH CAPSULES AND ONE OF THEIR PREPARATION METHODS

[75] Inventors: Rafael Jorda, Ste Fay les Lyons; Pierre Autant, Connentry; Rossin René, Oullins, all of France

[73] Assignee: Flamel Technologies, Venissieux Cedex, France

[21] Appl. No.: 80,767

[22] Filed: Jun. 24, 1993

[30] Foreign Application Priority Data

Jun. 24, 1992 [FR] France .................................. 92 07992

[51] Int. Cl.$^6$ ............................. B01J 13/02; B01J 13/04
[52] U.S. Cl. ........................ 264/4.1; 264/4.33; 424/405; 424/447; 424/484; 427/213.36
[58] Field of Search ..................................... 264/4.1, 4.33; 424/405, 447, 484; 427/213.38

[56] References Cited

U.S. PATENT DOCUMENTS 3,539,465  11/1970  Hiestand et al. ..................... 428/402.2
4,191,404   3/1980  Lee et al. ............................ 503/211
4,200,667   4/1980  Lee et al. ............................ 427/517

FOREIGN PATENT DOCUMENTS 0328335   8/1989  European Pat. Off. .
2808904   9/1978  Germany .
WO/03678  5/1989  WIPO .
9302668   2/1993  WIPO .

*Primary Examiner*—Nathan M. Nutter
*Attorney, Agent, or Firm*—Bacon & Thomas

[57] ABSTRACT

The invention relates to microcapsules containing at least one active ingredient, characterized in that they are constituted by:

an hydrophilic and essentially non-aqueous liquid inner core, formed of a solution of at least one active ingredient which is water-soluble and amphiphilic in at least one non-aqueous hydrophilic solvent, and by a wall, enclosing said inner core and based on at least one polymer or copolymer, and to one of their preparation methods.

The invention finds an application in systems of instant release of active ingredient, such as articles of hygiene, surgical gloves and materials.

30 Claims, No Drawings

MICROCAPSULES CONTAINING AT LEAST ONE ACTIVE INGREDIENT, APPLICATION OF SUCH CAPSULES AND ONE OF THEIR PREPARATION METHODS

FIELD OF THE INVENTION

The present invention relates to microcapsules containing at least one water-soluble and amphiphilic active ingredient, as well as to their applications, notably within a system of instant release of the active ingredient, such as by perforation, incision or crushing of the microcapsules.

The present invention also relates to one of the possible methods for preparing said microcapsules.

BACKGROUND OF THE INVENTION

The microcapsules are particles of substantially spherical shape, of size ranging between 1 and 2000 µm, comprising an inner core constituted by a solution or a dispersion of active ingredient and by an external envelope, generally based on polymers. Such microcapsules are of reservoir type.

Matrice-type microcapsules are also known, more commonly called microspheres, in which the active ingredient is dispersed throughout the particle, within a matrix constituted by a polymer acting as excipient.

The field of the invention is that of reservoir-type microcapsules.

A wide variety of active ingredients can be contained in the microcapsules. There may be medicines, such as antibiotics, virucides or hormones, or immunological agents, such as albumins, interferon, antigens or allergens, or even non-biological agents such as pesticides, detergents, pigments, catalysts or the like.

Said microcapsules can therefore be used in numerous fields such as pharmaceutics, bio-industry, cosmetology, agro-feeding, agro-chemistry, papermaking industry, etc. . .

In therapeutic applications, two methods are possible for using microcapsules.

The first one consists in the controlled and prolonged release of the active ingredient into the medium external to the microcapsule. Besides the requirements of biocompatibility and atoxicity, this using method presupposes that the polymeric external envelope is permeable to the active ingredient and that it allows the outward elution of the latter, according to given and constant kinetics, generally around zero. Said envelope should also be able to preserve its structural integrity against any chemical, biochemical or mechanical aggressions that it may be subjected to in its environment of use.

The second method exploits the capacity of the microcapsules to release instantly and massively the active ingredient, following a mechanical stress of the incision, perforation, crushing type, which induces the breaking, splitting or opening of their external envelope.

In this type of application, which is of particular interest to the invention, the microcapsules are required to have a breaking level which is especially adapted to the factors which will trigger the release of the active ingredient. The polymeric envelope should therefore be strong enough to prevent any premature releases and delicate enough to break up in the required circumstances.

The example whereby microcapsules are included in surgical gloves which are liable to be accidentally perforated by a needle, does illustrate this second method of use of the microcapsules.

Various methods are known which permit the microencapsulation of all types of active ingredients.

For example, U.S. Pat. No. 4,675,189 and European Patent Application No. EP 0 052 610, describe phase separation and coacervation techniques, consisting in using a coacervation agent such as mineral oils or vegetable oils.

Such techniques are very delicate to implement, due to the fact that they often give rise to the formation of cakes which make it difficult to obtain microcapsules.

According to other techniques, called polymerization or interfacial polycondensation techniques, two non-miscible liquid phases are mixed, one of which phases at least contains a polyfunctional reagent capable of inducing a polymerization, such as for example an isocyanate. A polymerization occurs at the interface of the two liquids in a reaction medium which may be an emulsion, then leading to the formation of microcapsules, the wall of which is formed of a polymer of polyamide, polyurethane, polyurea or polyester type.

Patent BE 796 746 describes the encapsulation of lipophilic active ingredients by polymerization of an isocyanate, in an oil-in-water emulsion, for obtaining microcapsules of which the wall is formed of polyurea.

Patent FR 2 548 046 relates to a similar method, permitting the encapsulation of water-soluble substances from an oil-in-water emulsion.

Patent application EP 0 407 257 relates to the encapsulation of water-soluble and amphiphilic substances, such as for example ammoniums, using said interfacial polymerization technique.

The interfacial polymerization is not among the best suited for these last compounds. Indeed, it requires the use of an inner core, as support for the amphiphilic substances, which is based on hydrophobic compounds and which contains high quantities of surface-active agents necessary for stabilizing the medium. Now, said latter do affect the action and efficiency of the active ingredient. Moreover, said surface-active agents do not really prevent the phenomena of agglutination noted during the preparation.

It should also be noted that, in said techniques, the inner core should not contain any products liable to impede the polymerization, for example by reacting with the polymerizing agents, such as the isocyanates. In particular, it is known that polyols, of polyethylene glycol, propylene glycol or glycerol type, are inappropriate as such.

Finally, the microcapsules obtained by this method have a wall which is mechanically inadapted for use with a system of massive and instant release of the active principle.

Other techniques for obtaining microcapsules rely on the formation of a simple oil-in-water emulsion or of a double water-in-oil-in-water emulsion and on the extraction of the solvent from the polymer, in order to solidify the latter. In effect, the polymer forms the phase known as "oily" phase of such emulsions.

In these types of techniques, the active ingredient is, either dispersed into the lipophilic phase containing the polymer in solution in an organic solvent (a simple oil-in-water emulsion), or contained in the internal aqueous phase $E_1$ of a double water-in-oil-in-water emulsion ($E_1/H/E_2$).

International Patent Application WO 90/13 381 describes a method using a double emulsion, in which a solution of polymer in an organic solvent is placed in contact with a non-amphiphilic active ingredient, optionally in aqueous medium, so as to form a first water-in-oil emulsion, called primary emulsion ($E_1/H$). Said latter is then introduced into a dispersing medium constituted, preferably, essentially of water and in which a secondary water-in-oil-in-water emulsion ($E_1/H/E_2$) can form.

According to this method or to other methods of double emulsion ($E_1/H/E_2$) type, the water is preferably used to constitute the internal aqueous phase of the primary $E_1$ emulsion. Water presents the advantage of being an economical, biocompatible, atoxic and ideal base material for the formation of emulsions. Appreciably, it is also, in most cases, inert and compatible towards water-soluble and amphiphilic active ingredients, with which the invention is more particularly concerned.

Yet, its use is not without raising problems with regard to the application of the microcapsules to systems of instant and massive release of the active ingredient, in which the active ingredient has to be very readily available and efficient towards the target.

Indeed, in this application, the microcapsules are embedded in an elastomer which forms the constituent material of the considered article, which may be surgical gloves. Now, crosslinking of the elastomer which occurs in the production of such articles, is achieved at high temperature, around 120° C. As a result, the inner aqueous core of the microcapsules containing the active ingredient evaporates, thus reducing considerably the efficiency of the active ingredient once the wall has been broken.

SUMMARY OF THE INVENTION

It is therefore an essential object of the present invention to provide microcapsules containing at least one active ingredient and constituted by an inner core containing said active ingredient and enclosed in a polymer-based wall, the encapsulated active ingredient being water-soluble and amphiphilic.

Another object of the invention is to provide microcapsules which can be applied in systems of instant and massive release of active principles and, in particular, in surgical gloves.

Another object of the invention is to provide microcapsules containing an amphiphilic active ingredient which are notably of constant quality, easy to obtain, made of materials compatible with the active ingredient, and temperature-stable.

These objects and more are attained with the microcapsules according to the invention which are, as new industrial products, microcapsules containing at least one active ingredient, characterized in that they are constituted by:
- a liquid inner core, which is hydrophilic and essentially non-aqueous, and formed of a solution of at least one water-soluble and active ingredient in at least one non-aqueous hydrophilic solvent,
- and by a wall, enclosing said inner core and containing at least one polymer or copolymer.

The presence of an hydrophilic and non-aqueous liquid inner core containing at least one water-soluble and amphiphilic active ingredient in solution in at least one non-aqueous hydrophilic solvent, constitutes a totally novel disposition of the invention.

According to the present invention, the term "essentially" means that the non-aqueous hydrophilic solvent is dominant in the solvent phase in question and, preferably, that the proportion of water in the solvent phase is under 50% by weight.

The microcapsules have homogeneous dimensions, with a mean diameter comprised between 50 and 2000 um, depending on the conditions of preparation. They are very suitable for applications to systems with instant release of active ingredient. They are indeed sufficiently elastic not to be crushed and to release the active ingredient that they contain only when a strong pressure has been applied, and not when they are just being handled. They are perfectly stable under air storage. No evaporation of the non-aqueous solvent in the inner core is observed. Moreover, said microcapsules have been found to be stable at high temperature (100° C.). The evaporation of the hydrophilic non-aqueous solvent is limited.

Such microcapsules are particularly well suited for external uses and they can be incorporated, non-restrictively, to papers, textiles (wovens or non-wovens), including bandaging materials (bandages, compresses) and fields of operation, to sponges and to polymer-based materials, in particular elastomers (gloves for medical or surgical use, preservatives), to nail-brushes (surgical brushes, for example), to disinfectant powders, etc. . .

The active ingredient is a water-soluble amphiphilic compound formed, preferably, by a quarternary ammonium. More preferably still, the amphiphilic compound is dimethyldidecylammonium.

According to the present invention, by dimethyldidecylammonium is meant both the basic product and its salts (halide, dihalide, organic salts for example).

It is indeed known that the quarternary ammoniums of dimethyldidecylammonium type are particularly advantageous in local applications as bactericides, fungicides and virucides. By way of example, it can be noted that the dimethyldidecylammonium has an efficient activity against the HIV virus.

Contrary to all expectations, the present invention makes it possible to avoid having to use water for the inner core of the microcapsules which, because of their hardness, do lend themselves to applications as systems with instant and massive release of active ingredients by perforation or crushing.

The products used in the preparation of the microcapsules according to the invention do not affect the activity of the active ingredient. Moreover, said ingredient is a water-soluble amphiphilic compound, and as such, it is known to favor the oil-in-water emulsions, whereas the microencapsulation requires water-in-oil-in-water type emulsions.

According to another advantageous characteristic of the invention, the concentration of active ingredient in the microcapsules ranges between 0.01 and 50% by weight, and is preferably between 0.1 and 15% by weight, and preferably still between 0.5 and 5% by weight.

To improve the thermal stability of the inner core of the microcapsules, the hydrophilic non-aqueous solvent advantageously has, under normal atmospheric pressure, a boiling point higher than 100° C., preferably higher than 120° C., and preferably still higher than 150° C. It is present in the microcapsules in the proportion of about 10 to 60% by weight.

According to a preferred disposition of the invention, the hydrophilic non-aqueous solvent is a compound or a mixture of compounds selected from the family of the polyols and/or hydroxyl polyethers, preferably from the following non-restrictive list of compounds:
  1–2 propanediol,
  polyethyleneglycol of molecular weight ranging preferably from 100 and 700,
  glycerol, the latter being particularly preferred.

The polymer is present in the microcapsules in the proportion of 20 to 90%, by weight, and preferably 40 to 70%.

According to another advantageous characteristic of the invention, said polymer is selected from the following products, used on their own or in combinations:

ethylene and vinyl acetate (EVA) copolymers, polystyrenes, polyesters, silicons, polymers and copolymers based on vinylidene chlorides and/or vinyl chlorides, polycarbonates.

In practice, it is preferred (without this being in any way restrictive) to use an ethylene and vinyl acetate (EVA) copolymer, the proportion of vinyl acetate of which, is preferably ranging between, 25 and 50%, and preferably still between 28 and 40%.

The present invention also provides a new method for the preparation of said microcapsules, of the type consisting in:

preparing a primary emulsion, of water-in-oil type ($E_1/H$), using a first hydrophilic phase $E_1$ and a second lipophilic phase H constituted by a solution of the polymer in at least one organic solvent, placing said primary emulsion in the presence of a third hydrophylic phase $E_2$, so as to form a secondary emulsion of water-in-oil-in-water type ($E_1/H/E_2$), and in removing the solvent from the polymer, so as to solidify the latter.

This new method is characterized in that:

the primary emulsion ($E_1/H$) is prepared with a solution or a dispersion A of the active ingredient in an hydrophilic non-aqueous solvent (first hydrophilic phase $E_1$) and of a composition B constituted by a solution of at least one polymer or copolymer in at least one organic solvent (second lipophilic phase H), said primary emulsion is placed in the presence of a fraction $C_1$ of a liquid hydrophilic composition C (third hydrophilic phase $E_2$) called dispersion and extraction composition, and containing at least two solvents $Sc_1$, $Sc_2$ which are miscible one with the other, one of said two solvents, $Sc_1$, being miscible with the solvent of the polymer, the other $Sc_2$, being non-miscible with said solvent and the polymer being non-soluble in $Sc_1$ and/or $Sc_2$, so as to form a secondary emulsion $E_1/H/E_2$ and, substantially simultaneously, to extract at least part of the solvent from the polymer, and a fraction $C_2$ of the composition C is added to complete the extraction and to induce the mass-setting of said polymer.

For the purpose of the invention, "non-soluble" designates a solubility preferably less than 1 g/l at a temperature of 25° C.

According to the invention, two liquids are considered as miscible if, and only if, they form, when mixed, one single phase in the proportions of the utilization.

It is preferable, on the one hand, that the active ingredient be non-soluble in the polymer solvent, so as to prevent it from migrating into the liophilic phase and, on the other hand, that the hydrophilic non-aqueous be non-miscible with the polymer solvent, so that the primary emulsion $E_1/H$ can form.

The dispersing and extractive composition C contains at least two solvents $Sc_1$, $Sc_2$ in which the polymer is not soluble.

$Sc_1$ is capable of carrying off the polymer solvent, whereas $Sc_2$ is not miscible with said polymer solvent.

The fact of providing two solvents, of which only one is active towards the solvent to be extracted, makes it possible to control the extraction speed and to overcome the problems of agglutination which are very frequent in this delicate technique of double emulsion.

$Sc_1$ and $Sc_2$ are found in the composition C according to a $Sc_1/Sc_2$ ratio which is so selected that the polymer fraction, extracted by composition C, is between 75 and 100%, and is preferably higher than 95% by weight in view of the initial total quantity of polymer solvent.

Preferably, the ratio $Sc_1/Sc_2$ is between 10 and 40% and more preferably still between 15 and 30% (volume/volume).

The solvents $Sc_1$ and $Sc_2$ are polar organic solvents.

$Sc_1$ may be selected among the alcohol, polyol and hydroxyl polyether families.

As to $Sc_2$, it can belong to the families of the following chemical compounds: polyols, hydroxyl polyethers.

In order to better prevent the agglutination problems, it is preferable to add to the composition C a dispersing and/or lubricating agent, such as talc.

According to an advantageous disposition of the method of the invention, the addition of the composition C to the primary emulsion $E_1/H$ takes place in fractions.

In practice, but non-restrictively, the composition C is divided into three sub-compositions $C'_1$, $C_1$ and $C_2$, which are successively incorporated to the primary emulsion $E_1/H$.

For example, the composition $C_1$ represents about 70% by volume of the composition C, the sub-composition $C'_1$ represents about 10% by volume, said sub-composition $C'_1$ advantageously containing a lubricating agent such as talc, and the composition $C_2$ represents about 20% by volume of the composition C.

The lubricating agent, which is optionally added in the composition C, is present at a concentration of about 1 to 7% by weight with respect to the microcapsules. According to a variant of the method, the elimination of the solvent from the polymer combines the solvent extraction technique described hereinabove with the evaporation technique.

The elimination of the solvent from the polymer by evaporation in the microencapsulation methods of the double emulsion $E_1/H/E_2$ type is a technique known per se. It is conceivable to use it on its own, without extraction of solvent.

The invention will be more readily understood and its advantages and variants of embodiment will emerge from the following examples.

EXAMPLES

Examples 1 to 9 illustrate the first method for the preparation of microcapsules according to the invention.

Examples 10 and 11 illustrate the second method.

Examples 12 to 15 illustrate the third method.

EXAMPLE 1

A. Materials:
  1. The active ingredient:
  The encapsulated active ingredient is dimethyldidecylammonium chloride ("BARDAC 22" LONZA - FRANCE). It is a quarternary ammonium salt, therefore it has all the properties of that chemical class:

It is a water-soluble cationic surface-active agent, with high wetting power. It is incompatible, notably with the anionic surface-active agents, such as soaps, divalent cations, silver nucleates and silver proteinates. It is adsorbed on elastomers.

It is an antiseptic and a disinfectant which is:
  very active on Gram$^+$ bacteria,
  active on Gram$^-$ bacteria, fungi and viruses (tetroviruses, in particular HIV),
  inactive on micobacteria and spores.

It can be applied on the skin (surgical approach, hands, wounds, burns) and on the conjunctival mucosa. The commercial aqueous solution is at 80%. The viscosity of the "BAROAC 22" solution is measured with a capillary viscosimeter at 20° C. (Ubbelohde tube). The viscosities obtained for solutions at 20%, 30% and 40% have respective values of 28, 38 and 47 cPs at 20° C.

2. The polymer:

The wall of the microcapsules is composed of EVA (ethylene/vinylacetate copolymer) containing 40 vinylacetate residues for 100 total residues ("ELVAX 40 W").

3. The compositions A, B and C:

| Composition A: | |
|---|---|
| glycerol (99% JANSSEN CHIMICA | 13.25 g |
| BARDAC 22 (LONZA) at 60% in water of dimethyldidecylammonium | 2.65 g |
| Erythrosin B (JANSSEN CHIMICA) | 0.10 g |
| Composition B: | |
| cyclohexane (LAURYLAB) | 69 ml |
| ELVAX 40 W (DUPONT DE NEMOURS) | 12 g |
| Composition C: | |
| 1-2 Propanediol (99% JANSSEN CHIMICA) | 454 cc |
| Butanol 1 (LAURYLAB) | 131 cc |
| Composition C gives three sub-compositions: | |
| $C_1$ or tank base: C | 350 cc |
| $C_1'$ or lubricant: C | 50 cc |
| officinal talc | 4 g |
| $C_2$ or addition | 185 cc |

B. Protocole:

1. Primary emulsion:

The solution A is added under stirring in a 150 ml Elermeyer flask, containing the composition B. Stirring is continued for 30 seconds at a speed of 800 rpm.

The size of the obtained emulsion is 5 to 100 µm.

2. Secondary emulsion:

The primary emulsion is poured quickly in the sub-composition $C_1$ or tank base, in a one-liter round-bottom reactor equipped with stirring means and with a pouring tube. The stirring speed is of 500 rpm. Then the sub-composition $C'_1$(or lubricant) is poured in, after what the solution $C_2$ starts to be added. This addition lasts between 20 and 30 mins. Stirring is kept up for 15 minutes once the sub-composition $C_2$ has been added in order to complete the extraction of the cyclohexane.

3. Treatment of the microcapsules:

filtration on a polyethylene cloth of 90 µm, two washes in 150 ml absolute ethanol, drying under an air stream.

C. Results:

The microcapsules obtained contain 53% of hydrophilic liquid, 1.8% of dimethyldidecylammonium with respect to the weight of the microcapsules.

The microcapsules do not dry up in the open and do not empty.

There is no bleeding of the inside liquid.

After 18 hours at 40° C., 37% of liquid is left.

After 56 hours at 40° C., 35% is still left.

After 2 hours at 100° C., 23% liquid is left inside the microcapsules.

Mean size of the capsules: Diameter N 400 µm

EXAMPLE 2

A composition A is prepared with 6.6 g of glycerol and 1.3 g of BARDAC 22.

A composition B is prepared with 6 g of ELVAX 240 (DUPONT DE NEMOURS) and 56.6 g of cyclohexane.

By applying the method described in Example 1, the obtained microcapsules are slightly smaller, with a diameter N of about 300 µm, than those obtained in Example 1.

The microcapsules contain 39% hydrophilic liquid.

EXAMPLE 3

The glycerol in composition A is replaced by 13.25 g of polyethylene glycol 400 (JANSSEN).

With the method described in Example 1, the microcapsules obtained are similar to those produced previously.

EXAMPLE 4

In composition C, the butanol.1 is replaced with 120 cc of propanol.2 (PROLABO).

The volume of composition $C_2$ (addition) is 174 cc.

The method used is identical to that of Example 1, and the size of the microcapsules obtained is slightly bigger than the size of the microcapsules obtained in Example 1.

EXAMPLE 5

Composition B contains 12 g of ELVAX 46 L (DUPONT DE NEMOURS) and 53.6 g of cyclohexane.

The microcapsules obtained according to the method described in Example 1, are more elongated in shape but their contents are identical to those obtained in Example 1. The stability of the microcapsules at 100° C. is better than that measured with the copolymer ELVAX 40 W.

EXAMPLE 6

The procedure is the same as in Example 1, except that the 12 g of ELVAX 40 W are replaced with 6 g of ELVAX 170 and that 53.6 g of cyclohexane are used. Also, half the quantity of solution A is used.

The shape of the obtained microcapsules is hardly spherical and their size ranges from 200 µm to 2000 µm.

Their contents are similar to those described in Example 1.

The ELVAX 170 has a better temperature stability than the ELVAX 40 W. Less flowing of the polymer is observed at 100° C.

EXAMPLE 7

The same materials and the same protocol are used as those used in Example 1, except that, in composition B, the cyclohexane is replaced by a 50/50 mixture of cyclohexane and hexane.

The primary emulsion obtained is centered around 10 um.

The microcapsules obtained are similar to those obtained in Example 1.

EXAMPLE 8

The method, in this example, changes slightly.

Composition $C_1$ is now constituted only of 400 cc of 1–2 propanediol. It no longer contains any butanol.1.

| Composition C₁': | |
|---|---|
| 1-2 propanediol | 54 cc |
| officinal talc | 4 g |

Composition $C_2$ is composed of the totality of the butanol.1 used, i.e. 131 cc.

The second emulsion is made in the composition $C_1$ and the extraction of the cyclohexane only starts when the composition $C_2$ has been poured in. This takes one hour and it takes half-an-hour to pour in the composition C'1. The microcapsules are bigger than in Example 1 (between 600 μm and 2000 μm) and contain as much of the hydrophilic liquids (approx. 50%) and of dimethyldidecylammonium (approx. 1%).

EXAMPLE 9

The same protocol and the same materials are used as in Example 1, except that the glycerol of composition A is replaced by 1-2 propanediol.

The obtained microcapsules are between 500 um and 800 um, and contain about 50% inner liquids.

After one hour at 40° C., 47% 1-2 propanediol is found in internal phase.

After 16 hours at 40° C., 39% internal liquid is still found. This percentage reduces only very little thereafter.

EXAMPLE 10

Reservoir-type microcapsules are produced by a solvent-evaporation method. In this method, the dispersing phase has no capacity of extraction towards the solvent of the coating polymer.

A primary emulsion is prepared by dispersion of a hydrophilic internal phase into an external phase containing the polymer in organic solution. This primary emulsion is then dispersed in a dispersing phase. The organic solvent is eliminated by evaporation in vacuo.
Primary emulsion:

| internal phase (E₁): | |
|---|---|
| glycerol | 18.3 g |
| BARDAC 2270 E (70% dimethyldidecyl-ammonium) | 9.2 g |
| aqueous solution at 10% by weight of RHODOVIOL 25/140 (RHONE-POULENC polyvinyl alcohol | 9.2 g |
| external phase (H) | |
| ELVAX 40 W | 18.3 g |
| dichloromethane | 165.1 g |

This primary emulsion is dispersed in:

| dispersing phase (E₂): | |
|---|---|
| demineralized water | 375 g |
| glycerol | 375 g |
| BARDAC 2270 E | 30 g |
| RHODOSIL 426 R silicon anti-foam (Rhône-Poulenc) | 2 ml |
| Addition at end of dispersion of: | |
| talc | 15 g |

The dichloromethane is evaporated under reduced pressure at room temperature, according to the following pressure sequence:

| under 460 mm Hg | 3 mins. |
|---|---|
| under 300 mm Hg | 5 mins. |
| under 160 mm Hg | 8 mins. |
| under 30 mm Hg | 1 hr. 10 mins. |

About 30 g of microcapsules are collected, which microcapsules have a diameter ranging from 100 to 315 μm, contain 6% of dimethyldidecylammonium chloride, and 26% of encapsulated liquid phase of which 62% of glycerol.

EXAMPLE 11

The method used in this example consists in cross-linking a silicon resin. An organic solvent is used for reducing the viscosity of the resin during the introduction into the reactor. The solvent is immediately eliminated by evaporation under reduced pressure and cross-linking of the resin is thereafter performed at a temperature ranging from 50° to 95° C.
Primary emulsion:

| internal phase (E₁): | |
|---|---|
| glycerol | 5 g |
| BARDAC 2270 E | 2.5 g |
| aqueous solution at 10% by weight of RHODOVIOL 25/140 | 2.5 g |
| external phase (H): | |
| silicon resin RTV 70141 A (RHONE POULENC) | 8 g |
| silicon resin RTV 70141 B (RHONE POULENC) | 2 g |
| dichloromethane | 15 g |
| propylene glycol dipelargonate (GATTEFOSSE) | 0.4 g |

This primary emulsion is dispersed in:

| dispersing phase (E₂): | |
|---|---|
| demineralized water | 360 g |
| aqueous solution at 10% by weight of RHODOVIOL 25/140 | 40 g |
| addition at end of dispersion of: | |
| silica (TixOSil 331) in suspension in | 5 g |
| demineralized water | 60 g |

The solvent is eliminated by distillation in vacuo (under 20 to 40 mm Hg), after what the cross-linking reaction is performed in one hour by heating to above 50° C.

EXAMPLE 12

In this example, reservoir-type microcapsules are produced according to a method which combines, simultaneously, the extraction and evaporation of the solvent from the coating polymer phase.

A primary emulsion composed of a hydrophilic internal phase and of an external phase containing a polymer in organic solution is dispersed in a dispersing phase which presents a capacity of extraction towards the solvent of the coating polymer. Such capacity of extraction is initially limited by partial solvent saturation. Progressive elimination of the solvent is thereafter continued by evaporation under reduced pressure.

Primary emulsion:

| internal phase (E₁): | |
|---|---|
| glycerol | 10 g |
| aqueous solution at 10% by weight of RHODOVIOL 25/140 | 5 g |
| external phase (H): | |
| ELVAX 40 W | 10 g |
| dichloromethane | 90 g |

This primary emulsion is dispersed in:

| dispersing phase: | |
|---|---|
| demineralized water | 173 g |
| polyethylene glycol PEG 200 | 403.5 g |
| dichloromethane | 173 g |
| Addition at end of dispersion of: | |
| talc (LUZENAC, STEAMIC OOS) | 7.5 g |

The dichloromethane is evaporated in vacuo at room temperature, in one hour according to the following pressure sequence:

| under 610 mm Hg | 15 mins. |
|---|---|
| under 460 mm Hg | 15 mins. |
| under 360 mm Hg | 15 mins. |
| under 260 mm Hg | 30 mins. |
| under 160 mm Hg | 15 mins. |

The product is recovered by filtration, washed in demineralized water and dried by fluidization at room temperature.

16 g of reservoir-type microcapsules are thus obtained, their diameter being about 400 μm, and their composition being as follows:

| dimethyldidecylammonium chloride content | 1% |
|---|---|
| external phase (coating) content of which 96.5% of ELVAX and 3.5% of talc | 57.8% |
| internal phase content of which 18% water and 82% of a mixture of glycerol and PEG. | 42.2% |

EXAMPLE 13

The method used in this example is that described in Example 12, except that the capacity of extraction of the PEG is limited by glycerol and a small quantity of BARDAC in dispersing phase is added in, so as to limit the exchanges with the hydrophilic internal phase.

Primary emulsion:

| internal phase (E₁): | |
|---|---|
| glycerol | 11.25 g |
| BARDAC 2270 E | 5.6 g |
| aqueous solution at 10% by weight of RHODOVIOL 25/140 | 5.6 g |
| external phase (H): | |
| ELVAX 40 W | 11.25 g |
| dichloromethane | 101.25 g |

This primary emulsion is dispersed in:

| dispersing phase (E₂): | |
|---|---|
| demineralized water | 510 g |
| glycerol | 127.5 g |
| PEG 300 | 112.5 g |
| BARDAC 2270 | 7.5 g |
| Addition at end of dispersion of: | |
| talc | 7.5 g |

The dichloromethane is evaporated under reduced pressure at room temperature, according to the pressure sequence described in example 12.

About 14 g of reservoir-type microcapsules are obtained after filtration, washing and drying, their diameter ranging from 100 to 400 um, and said microcapsules containing between 3 and 4.5% of dimethyldidecylammonium chloride, depending on the operational conditions, and having between 30 and 33% of encapsulated liquid phase constituted by 50 to 65% glycerol.

EXAMPLE 14

Using the method according to Example 13, reservoir-type microcapsules are produced by replacing the ELVAX 40 W with polystyrene (GEDEX 6519 JA NORSOLOR).

Primary emulsion:

| internal phase (E₁): | |
|---|---|
| glycerol | 5 g |
| BARDAC 2270 E | 2.5 g |
| aqueous solution at 10% by weight of RHODOVIOL 25/140 | 2.5 g |
| external phase (H): | |
| GEDEX 6519 JA 200 | 10 g |
| dichloromethane | 90 g |

This primary emulsion is dispersed in:

| dispersing phase: | |
|---|---|
| demineralized water | 460 g |
| glycerol | 115 g |
| PEG 300 | 100 g |
| BARDAC 2270 E | 7 g |
| Addition at end of dispersion of: | |
| talc | 7 g |

The dichloromethane is evaporated under reduced pressure at room temperature, according to the pressure sequence described in Example 12.

Microcapsules which have a diameter of 100 to 200 um, and contain 18% of encapsulated liquid phase, of which 89% glycerol, are thus obtained.

EXAMPLE 15

Reservoir-type microcapsules are produced according to the method described in Example 13, by replacing the ELVAX 30 W with a mixture of polyesters (copolymers DYNAPOL L 206/1 and DYNAPOL LS 415 of HULS).

Primary emulsion:

| internal phase (E$_1$): | |
|---|---|
| glycerol | 10 g |
| BARDAC 2270 E | 5 g |
| aqueous solution at 10% by weight of RHODOVIOL 25/140 | 5 g |
| external phase (H): | |
| DYNAPOL L 206/1 | 14 g |
| DYNAPOL LS 415 | 6 g |
| dichloromethane | 80 g |

This primary emulsion is dispersed in:

| dispersing phase (E$_2$): | |
|---|---|
| demineralized water | 460 g |
| glycerol | 115 g |
| PEG 300 | 100 g |
| BARDAC 2270 E | 7 g |
| Addition at end of dispersion of: | |
| talc | 7 g |

The dichloromethane is evaporated under reduced pressure at room temperature, according to the pressure sequence described in Example 12.

Microcapsules containing 26% of encapsulated liquid phase, of which 52% glycerol, are thus obtained.

What is claimed is:

1. Microcapsules containing at least one active ingredient, wherein said microcapsules are constituted by:

a liquid inner core, which is hydrophilic and essentially non-aqueous, and which is formed of a solution of at least one water-soluble and amphiphilic active ingredient in at least one non-aqueous hydrophilic solvent, and by a wall, enclosing said inner core and containing at least one polymer or copolymer.

2. Microcapsules as claimed in claim 1, wherein the non-aqueous hydrophilic solvent has a boiling point, under normal atmospheric pressure, which is higher than 100° C.

3. Microcapsules as claimed in claim 1, wherein the non-aqueous hydrophilic solvent is a compound or a mixture of compounds selected from the group consisting of polyols, hydroxyl polyethers or mixtures thereof.

4. Microcapsules as claimed in claim 1, wherein the amphiphilic active ingredient is a quartery ammonium.

5. Microcapsules as claimed in claim 1, wherein the active ingredient is present at a concentration ranging from 0.01 to 50% by weight.

6. Microcapsules as claimed in claim 1, wherein the polymer is selected from the following products, used on their own or in combinations: ethylene and vinyl acetate (EVA) copolymers, polystyrenes, polycarbonates, silicons, polymers or copolymers of vinylidene and/or vinyl chlorides, polycarbonates.

7. Microcapsules as claimed in claim 1, wherein the polymer is present in the proportion of 20 to 90% by weight.

8. Method for the preparation of microcapsules containing at least one active ingredient and constituted by:

a liquid inner core, which is hydrophilic and essentially non-aqueous, and which is formed of a solution of at least one water-soluble and amphiphilic active ingredient in at least one non-aqueous hydrophilic solvent, and by a wall, enclosing said inner core and containing at least one polymer or copolymer, whereby:

a primary emulsion, of water-in-oil (E$_1$/H), is prepared using a first hydrophilic phase E$_1$ and a second lipophilic phase H constituted by a solution of the polymer in at least one organic solvent, said primary emulsion is placed in the presence of a third hydrophylic phase E$_2$, so as to form a secondary emulsion of water-in-oil-in-water (E$_1$/H/E$_2$), and the solvent is removed from the polymer, so as to solidify the latter, method wherein:

the primary emulsion (E$_1$/H) is prepared with a solution or a dispersion A of the active ingredient in an hydrophilic non-aqueous solvent (first hydrophilic phase E$_1$) and of a composition B constituted by a solution of at least one polymer or copolymer in at least one organic solvent (second lipophilic phase H), said primary emulsion is placed in the presence of a fraction C$_1$ of a liquid hydrophilic composition C (third hydrophilic phase (E$_2$) called dispersion and extraction composition, and containing at least two solvents Sc$_1$, Sc$_2$ which are miscible one with the other, one of said two solvents, Sc$_1$, being miscible with the solvent of the polymer, the other Sc$_2$, being non-miscible with said solvent and the polymer being non-soluble in Sc$_1$ and/or Sc$_2$, so as to form a secondary emulsion E$_1$/H/E$_2$ and, substantially simultaneously, to extract at least part of the solvent of the polymer, and a fraction C$_2$ of the composition C is added to complete the extraction and to induce the mass-setting of said polymer.

9. Method as claimed in claim 8, wherein the two solvents (Sc$_1$, Sc$_2$) of composition (C) are present in a ratio (Sc$_1$/Sc$_2$) selected so that the fraction of the polymer solvent extracted by composition C is between 75 and 100% by weight with respect to the initial total quantity of solvent in the polymer.

10. Method as claimed in claim 8, wherein the addition of composition C to the primary emulsion (E$_1$/H) is performed in fractions.

11. Method as claimed in claim 8, wherein composition C comprises a dispersing agent and/or a lubricating agent, such as talc.

12. Method as claimed in claim 8, wherein the elimination of the solvent from the polymer involves extraction of the solvent and evaporation.

13. Papers or textiles containing microcapsules as claimed in claim 1.

14. Bandaging articles containing microcapsules as claimed in claim 1.

15. Products based on polymers, and particularly elastomers containing microcapsules as claimed in claim 1.

16. Gloves for medical or surgical use containing microcapsules as claimed in claim 1.

17. Preservatives containing microcapsules as claimed in claim 1.

18. Disinfectant powders containing microcapsules as claimed in claim 1.

19. Sponges containing microcapsules as claimed in claim 1.

20. Nail brushes, wherein they contain microcapsules as claimed in claim 1.

21. Microcapsules as claimed in claim 1 wherein the non-aqueous hydrophilic solvent has a boiling point, under normal atmospheric pressure, which is higher than 120° C.

22. Microcapsules as claimed in claim 1 wherein the non-aqueous hydrophilic solvent has a boiling point, under normal atmospheric pressure, which is higher than 150° C.

23. Microcapsules as claimed in claim 1, wherein the non-aqueous hydrophilic solvent is selected from the group consisting of 1–2 propanediol, polyethylene glycol having a molecular weight ranging from 100 to 700, and glycerol.

24. Microcapsules as claimed in claim 1, wherein the non-aqueous hydrophilic solvent is glycerol.

25. Microcapsules as claimed in claim 1, wherein the amphiphilic active ingredient is dimethyldidecylammonium.

26. Microcapsules as claimed in claim 1, wherein the active ingredient is present at a concentration ranging from 0.1 to 15% by weight.

27. Microcapsules as claimed in claim 1, wherein the active ingredient is present in a concentration ranging from 0.5 to 5% by weight.

28. Microcapsules as claimed in claim 1, wherein the polymer is a copolymer of ethyl and vinyl acetate.

29. Microcapsules as claimed in claim 1, wherein the polymer is present in a proportion of 40 to 70% by weight.

30. Microcapsules as claimed in claim 1, wherein the polymer is present at about 40% by weight.

\* \* \* \* \*